(12) United States Patent
Arbabian et al.

(10) Patent No.: US 9,544,068 B2
(45) Date of Patent: Jan. 10, 2017

(54) HYBRID COMMUNICATION SYSTEM FOR IMPLANTABLE DEVICES AND ULTRA-LOW POWER SENSORS

(71) Applicant: The Board of Trustees of the Leland Stanford Junior University, Palo Alto, CA (US)

(72) Inventors: Mohammad Amin Arbabian, San Francisco, CA (US); Marcus Weber, Palo Alto, CA (US); Jayant Charthad, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 303 days.

(21) Appl. No.: 14/276,827

(22) Filed: May 13, 2014

(65) Prior Publication Data

US 2014/0336474 A1 Nov. 13, 2014

Related U.S. Application Data

(60) Provisional application No. 61/822,763, filed on May 13, 2013.

(51) Int. Cl.
| | |
|---|---|
| *G08C 19/10* | (2006.01) |
| *H04B 11/00* | (2006.01) |
| *H02J 7/02* | (2016.01) |
| *H02J 17/00* | (2006.01) |
| *H04B 13/00* | (2006.01) |

(Continued)

(52) U.S. Cl.
CPC ............ *H04B 11/00* (2013.01); *A61B 5/0024* (2013.01); *A61B 5/0028* (2013.01); *A61B 5/686* (2013.01); *H02J 7/025* (2013.01); *H02J 17/00* (2013.01); *H04B 13/005* (2013.01); *A61B 5/0017* (2013.01); *A61B 5/0071* (2013.01); *A61B 5/0084* (2013.01); *A61B 5/01* (2013.01); *A61B 5/0538* (2013.01); *A61B 5/11* (2013.01);

(Continued)

(58) Field of Classification Search
CPC ... A61B 5/0031; A61B 5/6846; A61B 5/7232; A61B 10/02; A61B 1/00016; A61B 1/043; A61B 5/0071; A61B 5/0084; A61B 5/021; A61B 8/4472; A61B 1/0002; A61B 2560/0252; A61B 2560/0257; A61B 5/01; A61B 5/11; A61B 5/0538; A61B 5/686; A61B 5/0017; A61B 5/0024; A61B 5/0028; A61B 2560/0219; H04B 11/00; H04B 13/005; H02J 7/025; H02J 7/345; H02J 17/00
USPC ... 600/431, 486; 607/17, 61, 30, 33, 18, 35; 340/572.1, 539.22; 128/899, 903; 235/491; 427/2.24
See application file for complete search history.

(56) References Cited

U.S. PATENT DOCUMENTS

| | | | |
|---|---|---|---|
| 7,953,493 B2 | 5/2011 | Fowler et al. | |
| 2005/0099290 A1* | 5/2005 | Govari | A61B 5/06 340/539.13 |

(Continued)

*Primary Examiner* — Tesfaldet Bocure
(74) *Attorney, Agent, or Firm* — Lumen Patent Firm (57) ABSTRACT

Aspects of the present disclosure are directed toward apparatuses, systems, and methods that include a base unit and a communication circuit that communicate, while implanted in a patient, signals between the patient and at least one device located external to the patient. The base unit also includes a transducer that communicates ultrasound (US) signals between the base unit and the at least one device located external to the patient, and harvests energy carried by the US signals.

21 Claims, 7 Drawing Sheets

(51) Int. Cl.
    *A61B 5/00*     (2006.01)
    *A61B 5/01*     (2006.01)
    *A61B 5/11*     (2006.01)
    *A61B 5/053*     (2006.01)
    *A61B 5/145*     (2006.01)
    *H02J 7/34*     (2006.01)

(52) U.S. Cl.
    CPC ... *A61B 5/14503* (2013.01); *A61B 2560/0219* (2013.01); *H02J 7/345* (2013.01)

(56) References Cited

U.S. PATENT DOCUMENTS

2010/0324378 A1* 12/2010 Tran ................ A61B 5/0028
                                                        600/301
2013/0073003 A1* 3/2013 Pless ................ A61N 1/3785
                                                        607/61
2013/0178915 A1    7/2013 Radziemski et al.

\* cited by examiner

HYBRID COMMUNICATION SYSTEM FOR IMPLANTABLE DEVICES AND ULTRA-LOW POWER SENSORS

OVERVIEW

Aspects of the present disclosure are believed to be applicable to a variety of different types of devices, systems and arrangements involving low-power implantable devices and sensors. These devices and sensors can be used, for example, as medical implants and have a battery, no battery, or a minimal storage capacity (e.g., a super capacitor storage unit). Due to this low-power arrangement, power can be wirelessly delivered to the implantable devices and sensors. However, because the implantable devices and sensors are within the body, it is difficult to deliver effective signals to the implantable devices and sensor.

The above discussion/summary is not intended to describe each embodiment or every implementation of the present disclosure. The figures and detailed description that follow also exemplify various embodiments.

SUMMARY

Aspects of the present disclosure are directed toward apparatuses, systems, and methods that include data transfer and powering between an external device and (low-power) implantable packages and sensors. The present disclosure is exemplified in a number of implementations and applications, some of which are summarized below.

Various aspects of the present disclosure are directed toward apparatuses that include a base unit and a communication circuit that communicate, while implanted in a patient, signals between the patient and at least one device located external to the patient. In one such apparatus embodiment, an electrical circuit is secured by the base unit, and the electrical circuit includes at least one transducer, a capacitor circuit and a power circuit. In certain more specific embodiments, the electrical circuit can also include an antenna that is configured with the communication circuit to communicate RF signals between the base unit and the at least one device located external to the patient. The RF signals include downlink data from the device located external to the patient. The transducer communicates ultrasound (US) signals between the base unit and the device located external to the patient, and harvests energy carried by the US signals. In certain embodiments, the downlink data can also be carried over ultrasound signals.

The capacitor circuit stores the energy harvested by the transducer, and the power circuit powers-up the base unit based on the energy harvested by the transducer and stored by the capacitor circuit. Further, the power circuit prompts the communication circuit to transmit signals characterizing the patient's biological or physiological attribute to the device located external to the patient. Such communication occurs, in certain embodiments, via the antenna.

Aspects of the present disclosure are also directed towards methods that include a base unit and a communication circuit that communicate, while implanted in a patient, signals between the patient and at least one device located external to the patient. In one such embodiment, the method includes implanting the base unit including a communication circuit in the patient. The method also includes communicating, via an antenna configured with the communication circuit, RF signals between the base unit and the device located external to the patient including of downlink data from the external device, and communicating US signals between the base unit and the at least one device located external to the patient. Further, the method includes harvesting energy, via at least one transducer, carried by the US signals, and storing, via a capacitor circuit, the energy harvested by the transducer. Further, the method includes powering-up the base unit, via a power circuit, based on the energy harvested by the transducer and stored by the capacitor circuit, and prompting the communication circuit to transmit pulse-based signals characterizing the patient's biological or physiological attribute, via the antenna, to the at least one device located external to the patient.

The above discussion is not intended to describe each embodiment or every implementation. The figures and following description also exemplify various embodiments.

BRIEF DESCRIPTION OF THE DRAWINGS

Various example embodiments may be more completely understood in consideration of the following detailed description in connection with the accompanying drawings, and those in the Appendices as were filed as part of the underlying provisional application.

While the disclosure is amenable to various modifications and alternative forms, examples thereof have been shown by way of example in the drawings and will be described in detail. It should be understood, however, that the intention is not to limit the disclosure to the particular embodiments shown and/or described. On the contrary, the intention is to cover all modifications, equivalents, and alternatives falling within the spirit and scope of the disclosure.

DETAILED DESCRIPTION

The present disclosure is believed to be useful for data transfer and powering between a device that is external to a patient and one or more low-power devices (which can include one or more sensors) that are implanted in the patient. By utilizing a combination of US signals to power the low-power devices via an external device, the low-power devices can communicate with the external device using US and/or RF, which avoids degradation of the signals due to tissue (which can increase with signal frequency). In this manner, an effective amount of energy from the power signals provided to the low-power devices can be captured due to the dimensions of the power signals' wavelength. Such low-power devices can be used as medical implants for applications such as: pacemakers, glucose or electrolyte monitoring, neural recording, optogenetics (implanted sensors that emit light locally and can be programmed wirelessly), deep brain stimulation, peripheral nerve stimulation with implants (muscle or brain), pressure and/or temperature monitoring, blood pressure modulation, imaging, artificial organs, swallowable pill applications and cardiac mapping. While the present disclosure is not necessarily limited to such applications, various aspects of the disclosure may be appreciated through a discussion of various examples using this data transfer and powering context.

Various aspects of the present disclosure are directed toward apparatuses that include a base unit and a communication circuit that communicate, while implanted in a patient, signals between the patient and at least one device located external to the patient. The apparatuses can include an electrical circuit that is secured by the base unit. The electrical circuit includes an antenna, at least one transducer, a capacitor circuit, and a power circuit. The antenna is configured with the communication circuit to communicate RF signals between the base unit and the at least one device located external to the patient. The RF signals can also include downlink data from the device located external to the patient. The transducer communicates US signals between the base unit and the at least one device located external to the patient, and harvests energy carried by the US signals. The capacitor circuit stores the energy harvested by the transducer, and the power circuit powers-up the base unit based on the energy harvested by the transducer and stored by the capacitor circuit. Further, the base unit prompts the communication circuit to transmit signals characterizing the patient's biological or physiological attribute, via the antenna, to the at least one device located external to the patient.

Additionally, the communication circuit can also transmit the signals using a pulse-based communication scheme that includes periodic bursts of energy, that last less than 100 nanoseconds, at RF or microwave frequencies that are between 0.1 GHz and 10 GHz. In other embodiments, the pulsed-based communication scheme includes utilizing at least one of pulse position modulation (PPM), multi-PPM, pulse-amplitude modulation (PAM), and pulse width modulation (PWM). Further, in certain embodiments, the base unit also includes: an oscillator circuit that generates the pulse-based signals (e.g., an LC oscillator or ring-oscillator), a pulser circuit that modulates the pulse-based signals, and a power amplifier circuit that buffers the pulse-based signals and transmits the pulse-based signals via the antenna. Moreover, in other embodiments, the signals characterizing the patient's biological or physiological attribute are transmitted as active pulse signals, and the base unit also includes: an oscillator circuit that generates the active pulse transmission signals, a pulser circuit that modulates the active pulse transmission signals, and a power amplifier circuit that buffers the active pulse transmission signals and transmits the pulse-based signals via the antenna.

Certain apparatuses, methods, and systems also include the device being located external to the patient. Additionally, in certain embodiments, the base unit is arranged and sized to communicate with the device located external to the patient and other base units (that are similarly constructed) using a combination of RF and US signals. The base units and the device external to the patient can be synchronized based on communication notches in the US signal that are used to calibrate and correct for mismatch, delay, skew, or jitter in communication between the base units and the external device. The base unit can also include a light-emitting diode (LED) (or a laser diode) or other light source, and the power circuit powers-up the LED based on the energy stored by the capacitor circuit and activates the laser diode periodically or based on a pattern that is communicated to the base unit via the downlink data. Moreover, the base unit can include one or more of a chemical sensor, an impedance sensor, a fluorescence sensor, an optical sensor, temperature sensor, electrical voltage or spike sensors, and a vibrational sensor. In such embodiments, the power circuit powers-up and activates operational aspects of the sensor(s) included with the base unit. Additionally, in these embodiments, the base unit can use RF frequencies to transmit the pulse-based signals and uplink communication data indicative of the operation of the sensor from the base unit to the device located external to the patient. Moreover, in certain embodiments, the device located external to the patient transmits further downlink communication data indicative of a further operation of the sensor in response to receiving the uplink communication data indicative of the operation of the sensor from the base unit to the device located external to the patient.

In certain embodiments, the antenna, the transducer, the capacitor circuit, and the power circuit are provided as part of a silicon chip or integrated circuit. Additionally, in other embodiments, the transducer and the power circuit are provided as part of a silicon chip (or integrated circuit), and the antenna and the capacitor circuit are provided external to the silicon chip (or integrated circuit). Further, the capacitor circuit can include a piezoelectric or capacitive micro-machined transducer, and, in such embodiments, the US signal is converted into electrical energy, via the piezoelectric or the capacitive micro-machined transducer, and stored in the capacitor circuit.

The embodiments and specific applications discussed herein may be implemented in connection with one or more of the above-described aspects, embodiments and implementations, as well as with those shown in the appended figures.

Figure 1:
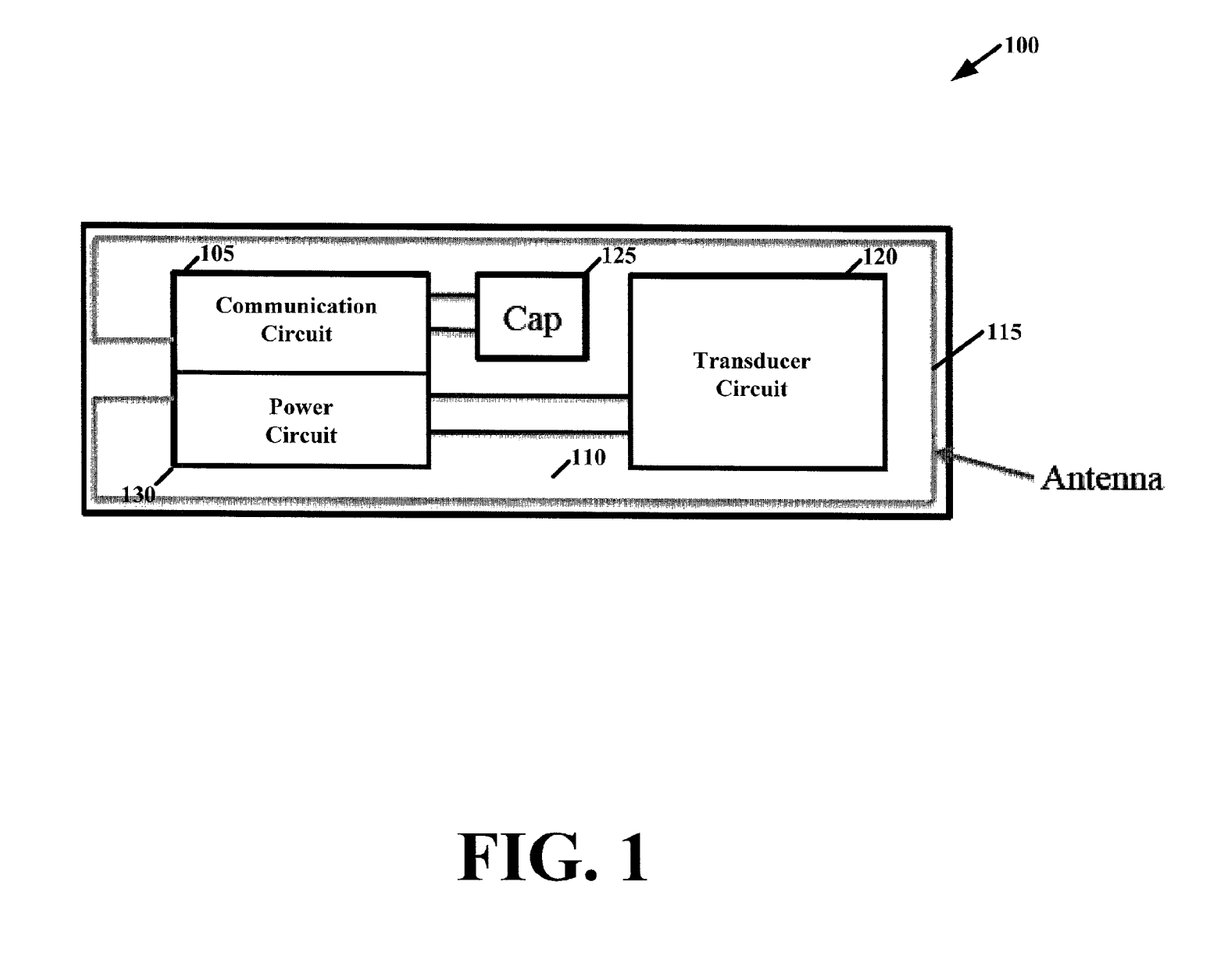
FIG. 1 shows a block diagram of an example base unit, consistent with various aspects of the present disclosure.

Turning now to the figures, FIG. 1 shows a block diagram of an example base unit 100 and communication circuit 105, consistent with various aspects of the present disclosure. The base unit 100 includes a communication circuit 105. The base unit 100 and the communication circuit 105 communicate, while implanted in a patient, signals between the patient and at least one device located external to the patient (e.g., as shown and discussed in further detail with reference to FIG. 4). Additionally, the base unit 100 also includes an electrical circuit 110 that is secured by the base unit 100. As shown in FIG. 1, the electrical circuit 110 can include an (optional) antenna 115 that is configured to the communication circuit 105 to communicate RF signals between the base unit 100 and the at least one device located external to the patient. The RF signals include downlink data from the device located external to the patient. The downlink data can also be carried over US signals. The electrical circuit 110 also includes a transducer circuit 120 that communicates US signals between the base unit 100 and the at least one device located external to the patient, and also harvests energy carried by the US signals. Further, the electrical circuit 110 includes a capacitor circuit 125 that stores the energy harvested by the transducer circuit 120. The electrical circuit 110 also includes a power circuit 130 that powers-up the base unit 100, based on the energy harvested by the transducer circuit 120 and stored by the capacitor circuit 125. Additionally, the power circuit 130 prompts the communication circuit to transmit signals characterizing the patient's biological or physiological attribute, via the antenna 115, to the at least one device located external to the patient. As discussed below in connection with FIG. 3, for example, one skilled in the art may appreciate that the base unit can have a sensor interface (and/or an actuator/stimulator) that is part of the base unit 100 and connected to the communication circuit 105 and/or power circuit 130. As noted below, the depiction of the antenna 115 in FIG. 1 is representative, and other shapes (and types) of antennas can be used.

As noted above, the (implanted) base unit 100 can communicate with the device located external to the patient and other base units (that are similarly constructed) that are also implanted in the patient using a combination of RF and US signals. Additionally, as noted above, the base unit(s) can include one or more sensors, with each base unit including the same or different types of sensors, which can be implanted at various places in the patient (including the brain).

Figure 2:
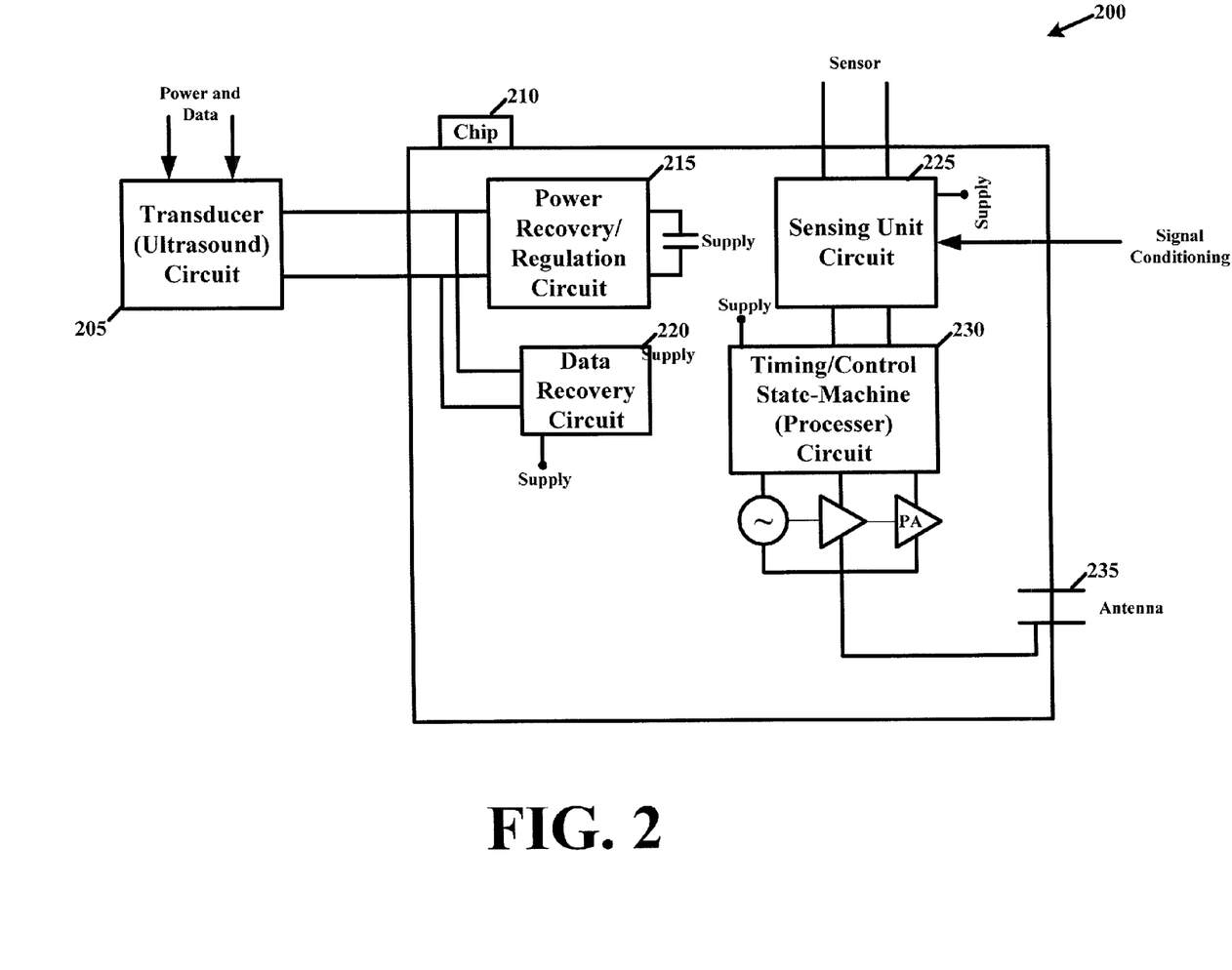
FIG. 2 shows another block diagram of an example base unit, consistent with various aspects of the present disclosure.

FIG. 2 shows another block diagram of an example base unit 200, consistent with various aspects of the present disclosure. The base unit 200 includes a transducer (ultrasound) circuit 205 and an integrated chip circuit 210 that includes a power recovery and regulation circuit 215, a data recovery circuit 220, sensing unit circuitry 225, timing/control processor circuitry 230, and circuitry for operating an RF antenna 235. The transducer (ultrasound) circuit 205 receives power and/or data signals provided in the form of US signal(s) from an external device, which will be passed to the power recovery and regulation circuit 215 as well as the data recovery circuit 220. The power recovery and regulation circuit 215 captures the power that is generated and received by the transducer (ultrasound) circuit 205, and also regulates the power that is provided to the remaining aspects of the integrated chip circuit 210. The data recovery circuit 220 receives the signals from the transducer circuit (ultrasound) 205, and passes the signals on if required. For instance, the data recovery circuit 220 can pass the data signals to the timing/control processor circuitry 230, which can activate the sensing unit circuitry 225. As discussed above, the sensing unit circuitry 225 controls and/or receives data from a sensor provided with the integrated chip circuit 210. Additionally, the integrated chip circuit 210 can communicate with external devices and/or other integrated chip blocks utilizing the circuitry shown for operating an RF antenna 235. The power recovery and regulation circuit 215 can also include an on-chip power supply (such as a battery) that can store the energy received by the transducer (ultrasound) circuit 205.

The timing/control processor circuitry 230 recovers the sensor output (data) from the sensing unit circuitry 225. Additionally, the timing/control processor circuitry 230 recovers timing data received from the downlinked signals from the data recovery circuit 220. The timing/control processor circuitry 230 also generates the modulated signals for RF transmission via the RF antenna 235. The timing/control processor circuitry 230 provides all timings, control, and duty cycles for the transmitted signals. The transducer (ultrasound) circuit 205 can include one or more transducers. In this manner, for example, the transducer (ultrasound) circuit 205 can have a dedicated transducer for downlink data and power, and a dedicated transmitter for uplink data (as described in further detail above).

Figure 3A:
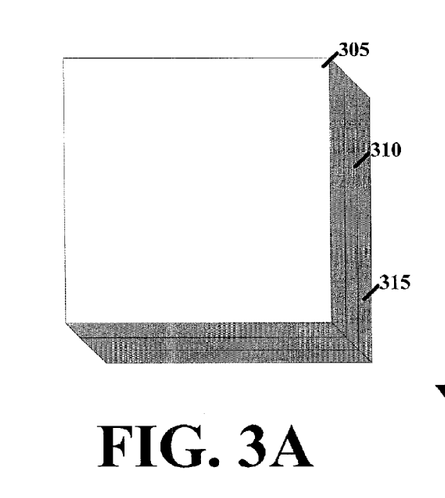
FIG. 3A-C shows example base units, consistent with various aspects of the present disclosure.
Figure 3B:
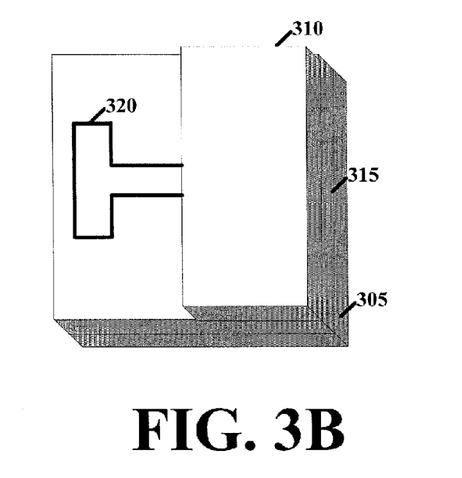
Figure 3C:
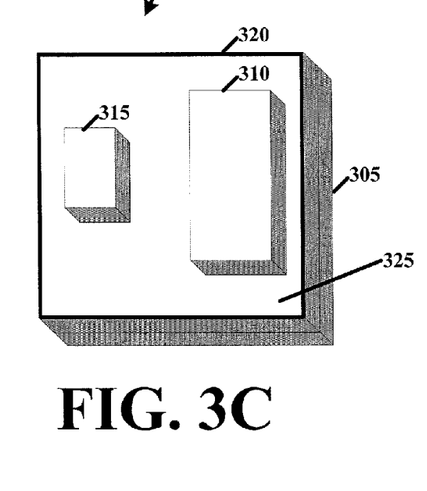

FIG. 3A-C shows example base units 300, consistent with various aspects of the present disclosure. Each of base units 300 includes a sensor interface 305, a silicon chip 310, and a transducer 315. Additionally, the base units 300 can also include a capacitor that can be on or off the silicon chip 310. The base unit shown in FIG. 3A includes a stack of the sensor interface 305, the silicon chip 310, and a transducer (the capacitor and an RF antenna are not shown). FIG. 3B shows a different example base unit 300 that also shows an RF antenna 320. FIG. 3C shows another different example base unit 300 base unit that includes the RF antenna 320 around the edge of a substrate 325.

Figure 4:
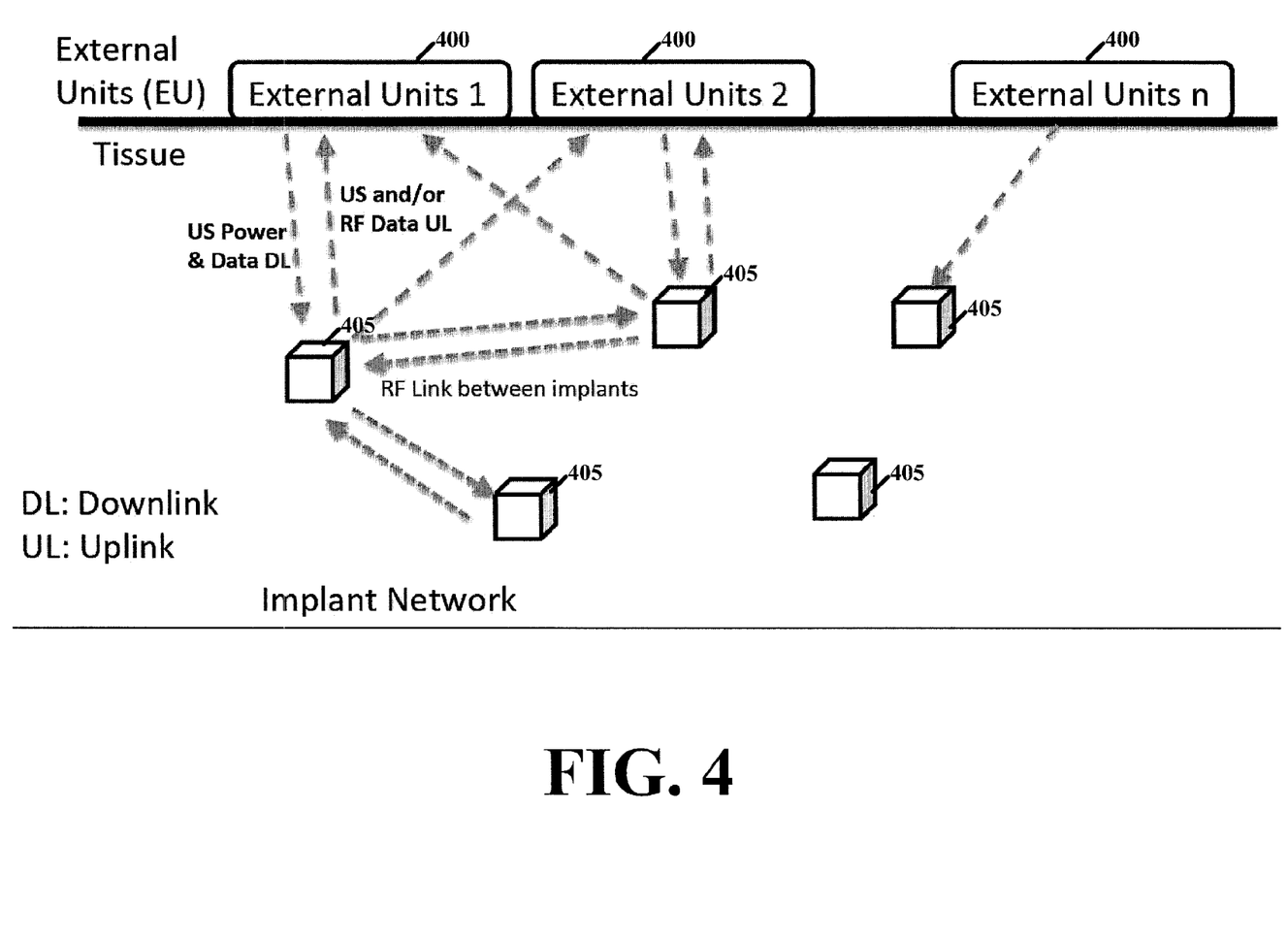
FIG. 4 shows an example network of devices 400 that are external to a patient (e.g., tissue) and base units 405, consistent with various aspects of the present disclosure.

FIG. 4 shows an example network of devices 400 that are external to a patient (e.g., tissue) and base units 405, consistent with various aspects of the present disclosure. As noted above, the base units 405, consistent with various aspects of the present disclosure, communicate with one or more devices 400 that are external to a patient. Additionally, the base units 405 can communicate amongst each other. In both instances, the communication is bidirectional (uplink and downlink). The downlink from the one or more devices 400 that are external to a patient and one or more of the base units 405 occurs using RF or US signals that include data. The uplink from the one or more devices 400 that are external to a patient and one or more of the base units 405 occurs using US signals and/or RF signals, which includes data. The communication between the base units 405 occurs via an RF link that carries RF signals.

Each of the base units 405 includes a unique address or a time window to transmit the signals. For example, one or more devices 400 that are external to a patient can communicate to one or more of the base units 405 using an allocation of the signal(s) based on slot, data and/or position. Additionally, the signal modulation can be in multiple-pulse pulse position modulation (MPPM) format, and each of the base units 405 can send multiple pulses to calibrate errors in the timing of the communication protocol. After one or more devices 400 that are external to a patient address and provide data to one or more of the base units 405, the signal position to the base units 405 can also be modulated based on the physical position of the base units 405 in the patient. This can be used for ranging/tracking of the base units 405 (e.g., the movement of the patient can shift the original position of the base units 405).

As noted above, the base units 405 can synchronize with one or more devices 400 that are external to a patient using periodic beacons sent from one or more devices 400 that are external to a patient. There is no explicit timing circuitry that is required for the base units 405 based on this synchronization capability. To reduce errors in communication, the base units 405 can send multiple calibration pulses to communicate the actual clock cycle to one or more devices 400 that are external to a patient. This eliminates the need for very high-accuracy clocks on the base units 405 (which can minimize the power needed) and eliminate issues of drift.

To facilitate the downlink power transfer from one or more of the devices 400 external to the patient to one or more of the base units 405, the US energy can be focused (either using an electronic beamforming array or by a passive acoustic lens) at the sites where the base units 405 are implanted in the patient. Additionally, as described above, feedback can be provide over the RF (up)link from one or more of the base units 405 to one or more of the devices 400 external to the patient. For example, US power can be gradually increased with feedback from the RF link. Once the position of the one or more of the base units 405 is identified based on this feedback, using ranging/tracking and determining the time of flight of the signal, US signal focusing will take place (with high power density). US energy will only be directed to positions of the base units 405 (or a focal volume that is set by the array).

Figure 5:
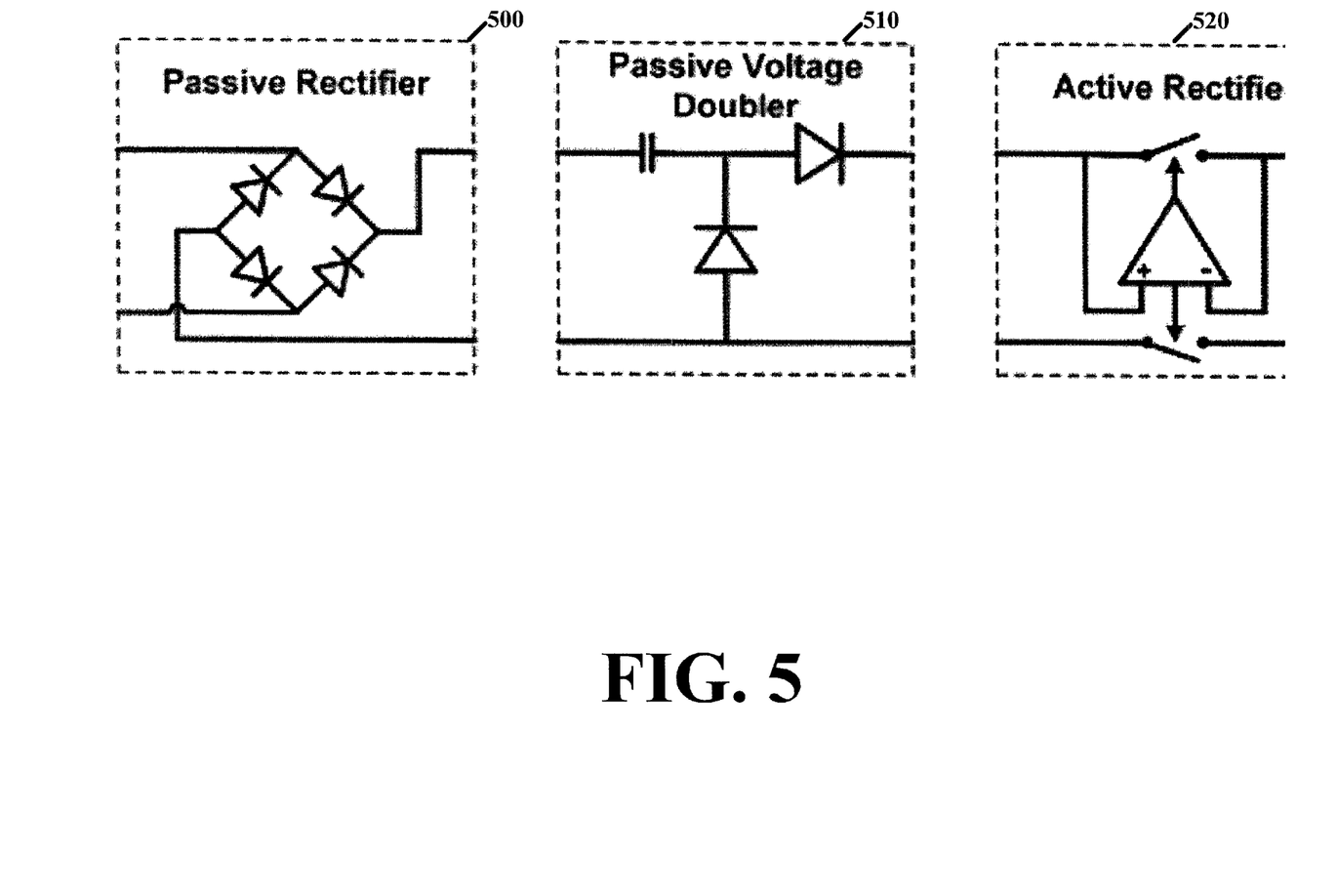
FIG. 5 shows example power harvesters, consistent with various aspects of the present disclosure.

FIG. 5 shows example power harvesters, consistent with various aspects of the present disclosure. The example power harvesters shown are a passive rectifier 500, a passive voltage doubler 510, and an active rectifier 520. One or more of the example power harvesters can be included with a base unit, consistent with various aspects of the present disclosure.

Figure 6:
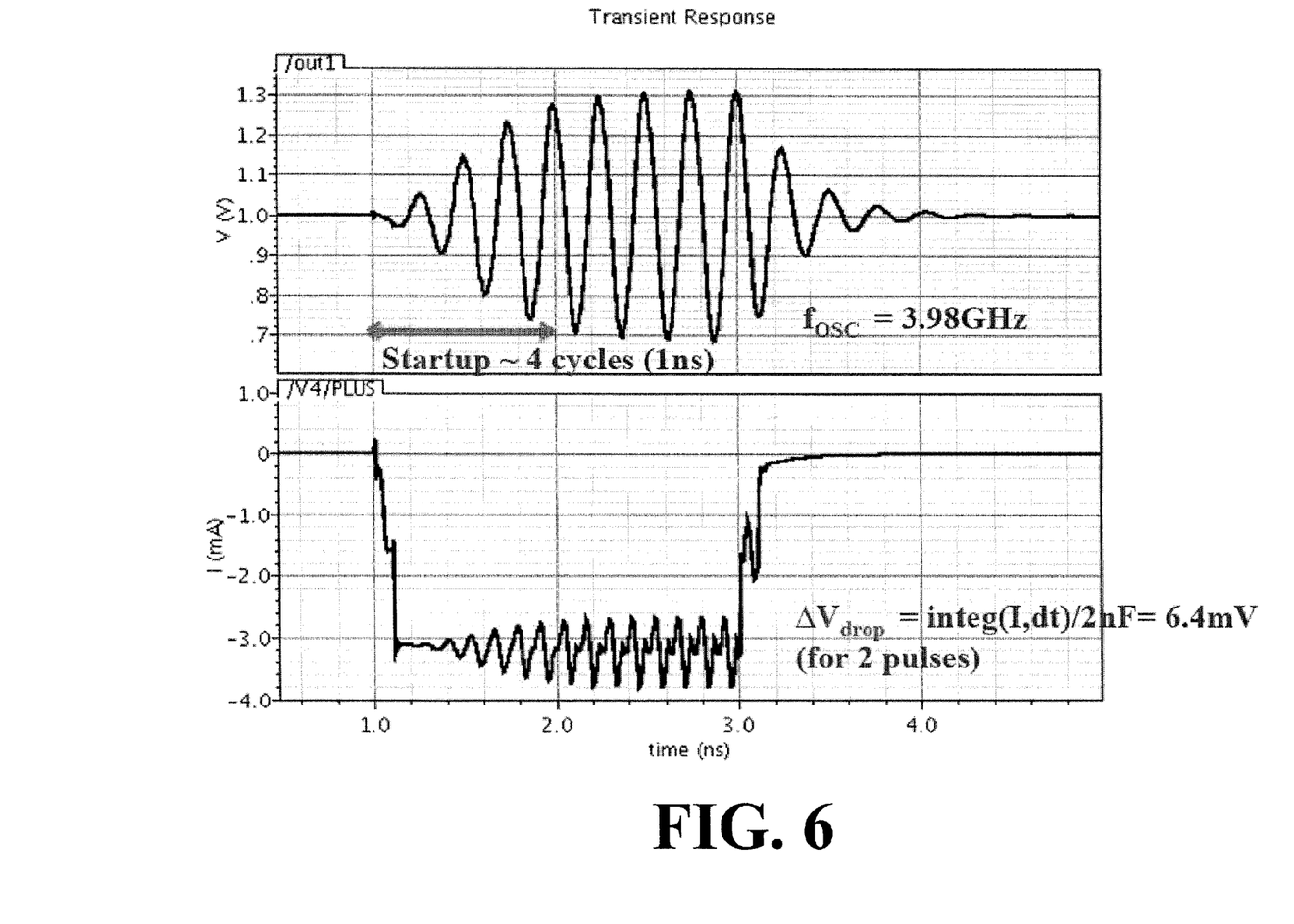
FIG. 6 shows an example transient response of a RF transmitter and a voltage drop, consistent with various aspects of the present disclosure.
Figure 7:
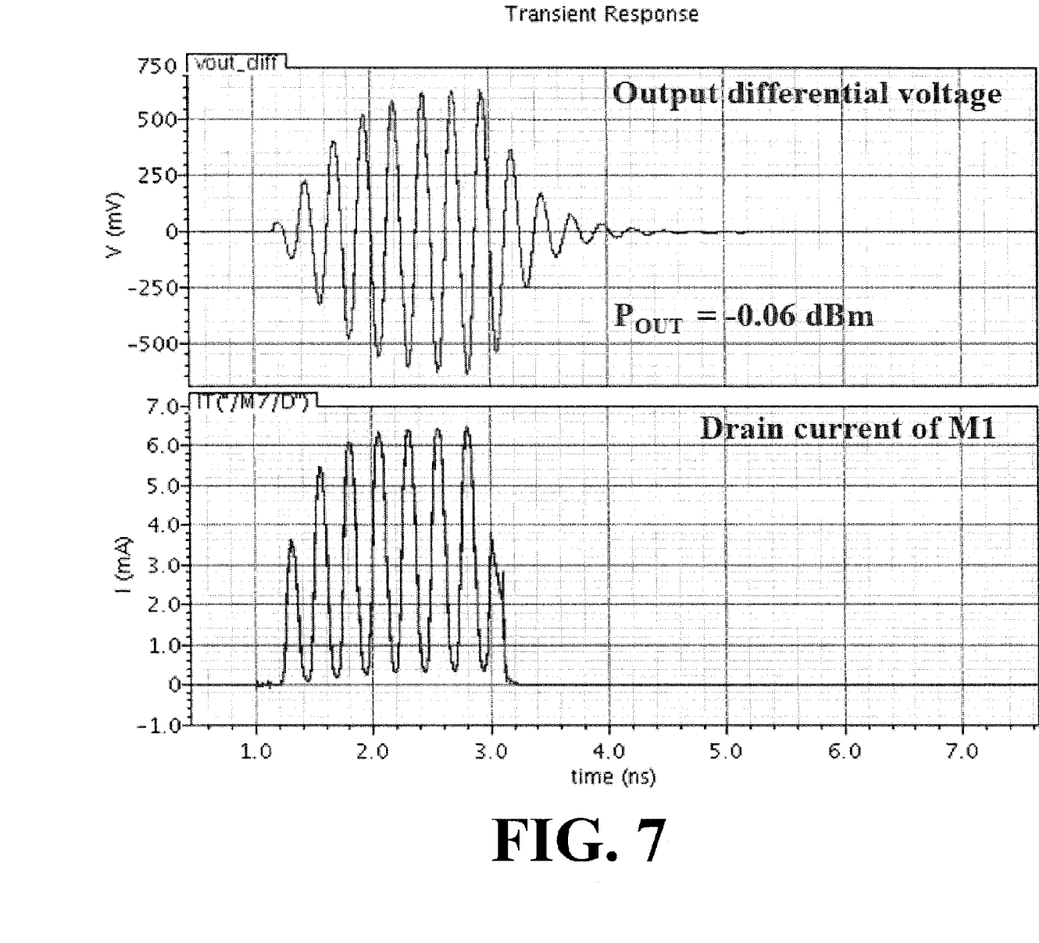
FIG. 7 shows an example output differential voltage of a base unit and drain current, consistent with various aspects of the present disclosure.

FIG. 6 shows an example transient response of an RF transmitter and a voltage drop, consistent with various aspects of the present disclosure. FIG. 7 shows an example output differential voltage of an implantable package and drain current, consistent with various aspects of the present disclosure.

As an example experimental budget link calculation, based on an order of magnitude per calculation, a base unit that does not include an external (additional) capacitor circuit is sized to include a 65 nm CMOS circuit. The total on-chip capacitor (storage) is approximately 1-5 nF, so it is reasonable to assume a total energy of approximately 1 nJ (for 2 nF capacitor charged to 1V). Typical duty-cycled RF pulses could consume approximately 1-100 mA current in active time and span from 0.1 to 100 (or even 1000) ns. Assuming a 10 mA current with a 2 ns pulse width, each pulse would draw approximately 20 pC of charge from the capacitor, which is 2% of the total stored charge. For charging using US, the power density of the signals is assumed to be 100 mW/cm². Thus, for a 1 mm² base unit, there is 1 mW of available power. Assuming 20% net efficiency, the charging power is 200 µW. So the time it takes for the capacitor circuit to recover the lost charge is approximately 100 ns, with a maximum duty cycle of 2%. Thus, if 5 pulses are transmitted (resulting in a 10% loss), the base unit will take 500 ns to recover its full power.

Various aspects of the present disclosure are also directed toward an apparatus or methods that include an implantable package that receives US acoustic waves from an external device, and converts those US acoustic waves into electrical energy. In certain more specific embodiments, the implantable package includes a piezoelectric or capacitive transducer to convert the US acoustic waves into electrical energy.

Aspects of the present disclosure are also directed toward an apparatus or methods that include an implantable package that communicates with an external device and/or other implantable packages or sensors using a combination of RF and US signals. The implantable package can communicate utilizing a pulse-based communication scheme that includes periodic (<100 nanosecond) bursts of energy at RF or microwave frequencies (0.1-10 GHz). Other forms of communication are also possible (e.g., Frequency-Shift Keying FSK).

Certain aspects of the present disclosure are also directed toward an apparatus or methods having an implantable package that utilizes a pulsed-based signaling timing to receive and convert US acoustic waves into electrical energy from an external device. Additionally, the implantable package communicates with the external device and/or other implantable packages or sensors using a combination of RF and US signals. In certain more specific embodiments, the pulsed-based signaling timing includes utilizing at least one of pulse PPM, multi-PPM, and PWM.

Various aspects of the present disclosure are directed toward an apparatus or methods that utilize an implantable package to communicate with an external device or other implantable packages or sensors using an active pulse transmission. More specifically and in certain embodiments, such an implantable package includes an antenna or transducer, and a local oscillator that generates active pulse transmission signals. Further, the implantable package also includes a pulser to modulate the active pulse transmission signals, and a power amplifier that buffers the active pulse transmission signals and transmits the active pulse transmission signals to the antenna or the transducer.

Moreover, aspects of the present disclosure are directed toward an apparatus or methods having an implantable package. The implantable package can communicate with an external device or other implantable packages or sensors, and also receive signals from the external device. The received signals include periodic beacons to synchronize the implantable package with the external device and other implantable packages or sensors. Further, in certain embodiments, the periodic beacons are used to synchronize all sensors or implantable packages and to calibrate and correct for any mismatch, delay, skew, or jitter.

Various aspects of the present disclosure are also directed toward an apparatus or methods that utilize an implantable package. The implantable package can include an integrated circuit as well as a capacitor (provided on the integrated circuit or provided external from the integrated circuit) that provides power to the integrated circuit to periodically transfer an active pulse from the implantable package. Further, the implantable package can include an antenna (external from the integrated circuit) that communicates with RF signals and/or an acoustic transducer that communicates with US signals to an external device in response to the power-up of the integrated circuit. Additionally, the implantable device can also include an acoustic transducer and interface that provides a power-up to the integrated circuit in response to an US signal provided from an external device. Implantable packages, consistent with various aspects of the present disclosure, can also include different types of sensors such as a chemical sensor, a molecular sensor, an impedance sensor, a fluorescence sensor, an optical sensor, a temperature sensor, and/or a vibrational sensor. Further, implantable packages can also include an LED or other light source, which is powered-up and modulated in response to signals received by the implantable package.

Various aspects of the present disclosure utilize directed US energy for remote power delivery to a sensor or implantable device or package. The US energy can act as the sole power-up scheme or to supplement the power from a RF power delivery system. In certain embodiments, the implantable device or package can include an antenna or a near-field element (loop or capacitor) for RF communication. The antenna or near-field element can be provided on the same chip or external to the chip on the common board or substrate. In such an embodiment, downlink data can be modulated on top of a carrier in the form of amplitude-shift keying (ASK), on-off keying (OOK), phase shift keying (PSK), or other types of suitable modulation schemes. Additionally, RF frequencies can be used for uplink communication from an implantable device or sensor to an external transceiver. This communication technique can also be used to compliment an US uplink. In this manner, a hybrid communication scheme can be formed that intelligently uses a combination of RF and US for power-up and communication. The active uplink pulse can be an RF pulse (typically with center frequency in the range of 0.1 GHz-10 GHz) or a US pulse actuated by a piezoelectric device or similar US transducers. The US pulse has a center frequency typically in the 100 KHz-100 MHz range and can be several cycles long (up to 1000's of cycles long).

Further, active pulse transmission (or backscatter) can be used for communication. In this manner, the charge or energy from the power delivery system (US or US-assisted) is stored on an on-chip or off-chip capacitor (e.g., typically 1 nF-100 µF depending on type of capacitor and implant size). This energy is used to periodically transmit an active pulse from the device.

Various implementations of the devices and/or sensors of the present disclosure can be implemented or packaged in a single millimeter-size "cube" that would include a chip, transducer(s), an energy storage unit, and one or more antennas. Uplink communication can use GHz frequency. In the wireless uplink channel, the external receiver can have a low noise floor in order to allow for a large dynamic range in the link. Losses in the order of 50-80 dB can be tolerated since the goal is not power delivery but communication. Thus, using RF for data uplink may not face the same challenges as for power delivery.

In certain embodiments, the RF link provides a high bandwidth in communication in the case of many implantable packages. This aids with both data rate (aggregate data rate from all implantable packages) as well as multiplexing/multi-access (fewer number of collisions in the shared channel). Further, the communications can be pulsed on the range of nanoseconds that provides heavy duty cycling, and therefore can provide high energy efficiency in the implantable package. This can allow for use of a single piezo element. Further, utilizing active pulse transmission can extend the operation range of the implantable package or sensor. The active pulse can have a peak power in the range of −50 dBm to 20 dBm (for implants this number is typically between −30 dBm and 0 dBm). The sensor can be integrated with other sensing and actuation elements. For example a fluorescence imager can be integrated in the package. Additionally, an array of LEDs or other light sources can be used for deep tissue implants in optogenetics. Glucose monitoring and insulin delivery can also be provided.

Various aspects of the present disclosure are directed toward a device or sensor that utilizes a piezoelectric or capacitive micro-machined transducer to convert acoustic waves into electrical energy. The electrical energy recovered by the transducer is stored on a capacitor and is used to operate the device. This operation includes communication, sensing, actuation, and stimulation by the sensor (e.g., using an LED or other light source to excite with light). The transmission is "wireless" and non-contact. The downlink communication (from external device to sensor) also takes place with this US wave. Depending on the application and to achieve higher data rates the downlink stream could also be using RF with a dedicated receiver chain that is powered up using the US signal through the power circuit. Different modulation schemes can be used to transmit this data (e.g., OOK on top of the incident US wave). Utilizing an US wave for power delivery, in certain embodiments, can assist in bringing the physical dimensions of the sensor (~1 mm0̂3 or even smaller) closer to the wavelength (acoustic wavelength is orders of magnitude shorter than electromagnetic wave due to lower wave velocity). This can allow the sensor to capture more of the incident energy with limited aperture. Additionally, acoustic propagation of US waves in human tissue can experience significantly lower loss compared to electromagnetic wave propagation (e.g., 1 dB/cm compared to >3-10 dB/cm for RF/electromagnetic wave in the low GHz frequency range). Moreover, US waves can be provided with a higher allowable power density than RF waves.

In certain embodiments, an US signal used for wireless power delivery to the base unit is provided by one or more ultrasonic transducers in an external device. An array of US transducers can be used to perform focusing by electronic beamforming. In the case of medical implants these external transducers will be external to the body and reside on the surface of the skin. On applications as in brain implants (e.g., closed-loop deep-brain stimulation (DBS)), these ultrasonic transducers can be intracranial implants and reside on the cortex itself That array and the electronics will then be powered up by another transcranial wireless link (either RF or US).

In other embodiments, base units, consistent with various aspects of the present disclosure, use an ultrasonic transducer to recover energy from the ultrasonic signal that is provided by the external units, and then use that energy to power up independent RF transmitter and/or receiver units that communicate with the external units and/or other base units in the environment. The communication may be duty-cycled and pulsed, and a large energy storage unit could be used to provide burst-mode energy for this type of communication.

More specifically, in certain embodiments, this transducer is used to harvest the energy carried by the US signals as well as to recover the downlink (DL) data that is sent to the base unit. This data can be modulated on the amplitude of the US signal. In another example and in case of using US for uplink, the base unit can transmit active US pulses using the acoustic transducer, or alternatively use backscatter modulation. If the same transducer is used for both downlink and uplink then a transmit/receiver switch or some form of time-multiplexing the two functions will be utilized.

For further discussion of implantable sensors, as relating to the embodiments and specific applications discussed herein, reference may be made to the underlying U.S. Provisional Patent Application Ser. No. 61/822,763 filed on May 13, 2013 (including the Appendices therein) to which priority is claimed and which are fully incorporated herein by reference generally and for the reasons noted above. The aspects discussed therein may be implemented in connection with one or more of embodiments and implementations of the present disclosure (as well as with those shown in the figures). Moreover, for general information and for specifics regarding applications and implementations to which one or more embodiments of the present disclosure may be directed to and/or applicable, reference may be made to the references cited in the aforesaid provisional application and Appendices, which are fully incorporated herein by reference generally and for the reasons noted above. In view of the description herein, those skilled in the art will recognize that many changes may be made thereto without departing from the spirit and scope of the present disclosure.

Various modules and/or other circuit-based building blocks may be implemented to carry out one or more of the operations and activities described herein and/or shown in the figures. In such contexts, a "module" is a circuit that carries out one or more of these or related operations/activities. For example, in certain of the above-discussed embodiments, one or more modules are discrete logic circuits or programmable logic circuits configured and arranged for implementing these operations/activities, as in the circuit modules shown in the figures (e.g., the power recovery/regulation circuit shown in FIG. 2). Additionally, one skilled in the art may appreciate that antennas shown in the figures (such as FIG. 1) are representative and can be formed of different shapes and/or sizes. In certain embodiments, the programmable circuit is one or more computer circuits programmed to execute a set (or sets) of instructions (and/or configuration data). The instructions (and/or configuration data) can be in the form of firmware or software stored in and accessible from a memory (circuit). As an example, first and second modules include a combination of a CPU hardware-based circuit and a set of instructions in the form of firmware, where the first module includes a first CPU hardware circuit with one set of instructions and the second module includes a second CPU hardware circuit with another set of instructions.

Certain embodiments are directed to a computer program product (e.g., nonvolatile memory device), which includes a machine or computer-readable medium having stored thereon instructions which may be executed by a computer (or other electronic device) to perform these operations/ activities.

Based upon the above discussion and illustrations, those skilled in the art will readily recognize that various modifications and changes may be made to the present invention without strictly following the exemplary embodiments and applications illustrated and described herein. For example, the input terminals as shown and discussed may be replaced with terminals of different arrangements, and different types and numbers of input configurations (e.g., involving different types of input circuits and related connectivity). In addition, resistors of various values may be used in the input state detection circuits as shown and described, together with different values of Vdd, as relative to other resistors in the circuit and/or of the input circuits of which the resulting input pin state is to be evaluated. Such modifications do not depart from the true spirit and scope of the present invention, including that set forth in the following claims.

What is claimed is:

1. A hybrid ultrasound and RF communication link, comprising:
    a base unit, wherein said base unit is implantable to a host, wherein said base unit comprises:
    i. an ultrasound transducer circuit, wherein said ultrasound transducer circuit is disposed to receive ultrasound signals from a device that is external to said base unit, wherein said ultrasound transducer circuit is configured to convert said ultrasound signals into electrical signals, and to harvest energy carried by said ultrasound signals, wherein said ultrasound signals comprise data, power, or data and power;
    ii. a power recovery circuit, wherein said power recovery circuit is disposed to receive said electrical signals from said ultrasound transducer circuit, wherein said power recovery circuit is disposed to power said base unit;
    iii. a capacitor circuit, wherein said capacitor circuit is disposed to store the energy harvested by said ultrasound transducer circuit;
    iv. an antenna circuit, wherein said antenna circuit comprises an RF antenna or a second ultrasound transducer, wherein said antenna circuit is disposed to transmit, receive, or transmit and receive RF signals, said ultrasound signals, or said RF signal and said ultrasound signal;
    v. a data recovery circuit, wherein said data recovery circuit is disposed to receive said ultrasound signals from said ultrasound transducer circuit, wherein said data recovery circuit is disposed to receive other said ultrasound signals from a second ultrasound transducer circuit, wherein said data recovery circuit is disposed to receive said RF signals from said RF antenna;
    vi. a communication circuit, wherein said communication circuit is disposed to transmit said RF signals or transmit said ultrasound signals to communicate with said device that is external to said base unit, or communicate with other said base units, or communicate with said device that is external to said base unit and other said base units through said antenna circuit; and
    b. an external unit, wherein said external unit is external to said host, wherein said external unit is disposed to deliver power to said base unit, wherein said external unit is disposed to communicate with said base unit using said ultrasound signals, said RF signals, or said ultrasound signals and said RF signals.

2. The hybrid ultrasound and RF communication link according to claim 1 further comprises a sensing unit circuit, wherein said sensing unit circuit controls, receives, or controls and receives data from a sensor configured with said sensing unit circuit, wherein said sensing unit circuit is configured to output a tissue stimulation signal.

3. The hybrid ultrasound and RF communication link according to claim 2, wherein said tissue stimulation signal is selected from the group consisting of a light signal, an electrical signal, a vibration signal and an acoustic signal, wherein said tissue stimulation signal from said sensing unit is output periodically or based on a pattern that is communicated to said base unit via downlink data.

4. The hybrid ultrasound and RF communication link according to claim 2 further comprises a timing and control processor circuit, wherein said timing and control processor circuit is disposed to receive said ultrasound signals, said RF signals, or said ultrasound signal and said RF signal, from said data recovery circuit, wherein said received data signals are configured to activate said sensing unit circuit.

5. The hybrid ultrasound and RF communication link according to claim 4, wherein said power recovery circuit, said capacitor circuit, said data recovery circuit, said timing and control processor circuit, said sensing unit circuit, and said communication circuit are part of an integrated circuit chip.

6. The hybrid ultrasound and RF communication link according to claim 5, wherein said power recovery circuit, said data recovery circuit, said timing and control processor circuit, said sensing unit circuit, and said communication circuit are part of an integrated circuit chip, wherein said capacitor circuit is outside said integrated circuit chip.

7. The hybrid ultrasound and RF communication link according to claim 1, wherein said base unit comprises a unique address or uses a unique time window to transmit said RF signals, said ultrasound signals, or said RF signals and said ultrasound signals.

8. The hybrid ultrasound and RF communication link according to claim 1, wherein said base unit and said external unit are synchronized according to communication notches in said ultrasound signal, wherein said communication notches are capable of correcting for mismatch, delay, skew or jitter in communication between said base unit and said external unit.

9. The hybrid ultrasound and RF communication link according to claim 1, wherein said base unit and said external unit are synchronized according to periodic beacons or multiple calibration pulses without requiring an explicit timing synchronization circuitry.

10. The hybrid ultrasound and RF communication link according to claim 4, wherein said timing and control processor circuit is further configured to generate modulated signals for RF or ultrasound transmission by said antenna circuit.

11. The hybrid ultrasound and RF communication link according to claim 4, wherein said timing and control processor circuit is configured to generate timings, controls, and duty cycles for said transmitted RF or said ultrasound signals.

12. The hybrid ultrasound and RF communication link according to claim 4, wherein said timing and control processor circuit is configured to modulate pulse-based signals for transmission, wherein said transmitted signals are pulse-based or duty-cycled.

13. The hybrid ultrasound and RF communication link according to claim 1, wherein said communication circuit is configured to transmit signals using a pulse-based communication scheme, wherein said pulse-based communication scheme comprises periodic bursts of energy.

14. The hybrid ultrasound and RF communication link according to claim 13, wherein said pulse-based communication scheme comprises modulation schemes selected from the group consisting of pulse position modulation (PPM), multi-PPM, pulse-amplitude modulation (PAM), and pulse width modulation (PWM).

15. The hybrid ultrasound and RF communication link according to claim 1, wherein said ultrasound transducer circuit is configured to uplink, downlink, or uplink and downlink said ultrasound signal between said base unit and said external unit.

16. The hybrid ultrasound and RF communication link according to claim 1, wherein said ultrasound signal is uplinked from said base unit to said external unit according to said ultrasound transducer circuit.

17. The hybrid ultrasound and RF communication link according to claim 1, wherein said external unit comprises an array of said external units.

18. The hybrid ultrasound and RF communication link according to claim 1, wherein said base unit comprises an array of said base units.

19. The hybrid ultrasound and RF communication link according to claim 18, wherein one said base unit is configured to communicate with another said base unit using RF communication.

20. The hybrid ultrasound and RF communication link according to claim 1, wherein said RF signals and said ultrasound signals comprise downlink data and uplink data between said base unit and said external unit.

21. The hybrid ultrasound and RF communication link according to claim 1, wherein said capacitor circuit has a range of capacitance of 1 nF-100 μF.

* * * * *